United States Patent
Choubey

(10) Patent No.: US 7,451,002 B2
(45) Date of Patent: Nov. 11, 2008

(54) AUTOMATED GENERATION OF TRANSFER FUNCTIONS BASED UPON MACHINE DATA

(75) Inventor: Suresh Kumar Choubey, Delafield, WI (US)

(73) Assignee: GE Medical Systems Global Technology Company, LLC, Milwaukee, WI (US)

( * ) Notice: Subject to any disclaimer, the term of this patent is extended or adjusted under 35 U.S.C. 154(b) by 220 days.

(21) Appl. No.: 11/326,891

(22) Filed: Jan. 6, 2006

(65) Prior Publication Data

US 2007/0162190 A1    Jul. 12, 2007

(51) Int. Cl.
| | |
|---|---|
| G05B 11/01 | (2006.01) |
| G05B 9/02 | (2006.01) |
| G01D 3/00 | (2006.01) |
| G01M 19/00 | (2006.01) |
| G01P 21/00 | (2006.01) |
| G01R 35/00 | (2006.01) |
| G06F 19/00 | (2006.01) |
| G06F 11/00 | (2006.01) |
| G01C 25/00 | (2006.01) |
| A61B 5/00 | (2006.01) |
| A61B 19/00 | (2006.01) |
| G08B 29/00 | (2006.01) |
| A61N 1/00 | (2006.01) |

(52) U.S. Cl. ............... 700/21; 700/79; 702/109; 702/116; 702/184; 600/300; 607/27; 607/30; 607/32; 340/516; 128/898

(58) Field of Classification Search .......... 607/17, 607/26–32, 60; 600/300, 301, 407, 513; 340/870.01, 870.04, 870.07, 870.16, 500, 340/501, 540, 514, 516; 700/17, 19, 21, 700/65, 79, 83, 90, 81; 702/117, 182–185, 702/187, 188, 108, 109, 116; 705/2; 709/217, 709/223, 224; 128/897–899; 714/1, 27, 714/30, 37, 47

See application file for complete search history.

(56) References Cited

U.S. PATENT DOCUMENTS

| | | | | | |
|---|---|---|---|---|---|
| 5,014,208 | A | * | 5/1991 | Wolfson | 700/99 |
| 5,685,314 | A | * | 11/1997 | Geheb et al. | 600/513 |
| 5,807,336 | A | * | 9/1998 | Russo et al. | 604/131 |
| 5,860,918 | A | * | 1/1999 | Schradi et al. | 600/300 |
| 6,101,407 | A | * | 8/2000 | Groezinger | 600/407 |
| 6,192,283 | B1 | * | 2/2001 | Holowko | 700/28 |
| 6,350,237 | B1 | * | 2/2002 | Pelletier et al. | 600/300 |
| 6,442,433 | B1 | * | 8/2002 | Linberg | 607/60 |
| 6,494,831 | B1 | * | 12/2002 | Koritzinsky | 600/301 |
| 6,751,630 | B1 | * | 6/2004 | Franks et al. | 707/102 |
| 6,898,463 | B2 | * | 5/2005 | Dropps et al. | 607/27 |
| 7,041,941 | B2 | * | 5/2006 | Faries et al. | 219/413 |

(Continued)

*Primary Examiner*—Crystal Barnes Bullock
(74) *Attorney, Agent, or Firm*—Fletcher Yoder

(57) ABSTRACT

A system and method for servicing a medical device, which provides for generation of a transfer function that correlates historical machine data with the health of the medical device. The transfer function may be validated and stored. The transfer function is automatically updated based on current machine data.

23 Claims, 5 Drawing Sheets

U.S. PATENT DOCUMENTS

| | | | |
|---|---|---|---|
| 7,072,725 B2 * | 7/2006 | Bristol et al. | 700/90 |
| 7,107,185 B1 * | 9/2006 | Yemini et al. | 702/183 |
| 7,256,708 B2 * | 8/2007 | Rosenfeld et al. | 340/870.01 |
| 7,289,761 B2 * | 10/2007 | Mazar | 455/1 |
| 2003/0135087 A1 * | 7/2003 | Hickle et al. | 600/26 |
| 2004/0138920 A1 * | 7/2004 | Sawanaga et al. | 705/2 |
| 2004/0153289 A1 * | 8/2004 | Casey et al. | 702/188 |
| 2004/0153437 A1 * | 8/2004 | Buchan | 707/1 |
| 2004/0176929 A1 * | 9/2004 | Joubert et al. | 702/184 |
| 2005/0103354 A1 * | 5/2005 | Miyauchi et al. | 128/898 |
| 2005/0283210 A1 * | 12/2005 | Blischak et al. | 607/60 |
| 2006/0079310 A1 * | 4/2006 | Friedman et al. | 463/16 |
| 2006/0122481 A1 * | 6/2006 | Sievenpiper et al. | 600/407 |
| 2007/0038402 A1 * | 2/2007 | Zhang | 702/117 |
| 2007/0106129 A1 * | 5/2007 | Srivathsa et al. | 600/300 |

* cited by examiner

AUTOMATED GENERATION OF TRANSFER FUNCTIONS BASED UPON MACHINE DATA

BACKGROUND

The invention relates generally to the field of medical electronic device operation and maintenance. More particularly, the invention relates to a system and method for establishing predictive maintenance of such devices based on automatically updated transfer functions that correlate device health with device parameters.

There are many different medical electronic devices available for learning about and treating patient conditions in the medical field. For example, over recent decades, more sophisticated systems have been developed that include various types of electrical data acquisition which detect and record the operation of systems of the body and, to some extent, the response of such systems to situations and stimuli. Even more sophisticated systems have been developed to provide images of the body, including internal features which could only be viewed and analyzed through surgical intervention before their development. In general, such techniques have added to the vast array of resources available to physicians, and have greatly improved the quality of medical care.

However, medical devices, such as medical imaging systems, are generally complex. The complexity of medical devices makes identifying and correcting problems with the devices difficult and time-consuming. Further, servicing of medical devices tends to be reactive, after the medical device has failed, resulting in unscheduled downtime and added costs. In the case of medical imaging systems, for example, image quality may unexpectedly fall below acceptable levels, requiring an unscheduled shutdown of the medical imaging system. As appreciated by those skilled in the art, unscheduled downtime results in inefficient and costly operation of the medical system, costly repair, and inconvenience to patients, and so on. This impacts a variety of entities, such as medical providers, patients, equipment service providers, and so forth.

In an effort to avoid unexpected machine failures, a preventative maintenance schedule may be implemented where medical devices are serviced on a periodic basis. Such preventative services may include part replacement, component calibration, and so on, and may be primarily a function of the brand or type of medical device. Indeed, the period of maintenance and selected component replacement may be based on the device type and may not reflect the actual usage of the device and the environment in which the medical devices are deployed.

Consequently, periodic maintenance may result in over-servicing or under-servicing of the device. In either case, the result may be increased costs, a missed opportunity to improve the service delivery cost, and so on. Generally, devices are not utilized in the same way and/or are typically not stressed to the same extent. Thus, all devices do not benefit from service and same interval of service. Generic maintenance approaches may not consider the operational and maintenance history of the specific device, resulting in inappropriate service of the actual medical system. Preventative maintenance frequently results in unnecessary service of properly-functioning medical systems and devices. While preventative maintenance may reduce unscheduled downtime, the types and timing of services under a preventative maintenance schedule commonly do not match the needs of the medical system or device.

Unfortunately, is common for a maintenance schedule to be based on the type of modality or device without taking into account the device environment. In sum, such a maintenance schedule often calls for repair of the device where repair is not needed. Clearly, unnecessary and/or inappropriate services increase the cost to operate and maintain medical devices. A need, therefore, exists for a technique to identify the appropriate types and timing of services of a medical system or device. Servicing of the medical systems should deliver high quality of performance and uptime without unnecessary part replacement or costs.

BRIEF DESCRIPTION

In one aspect of the present technique, a method of maintaining a medical device or system includes generating a transfer function correlating historical machine data with a health of the medical device, and validating and storing the transfer function. The method further includes receiving current machine data of the medical device in substantially real time and automatically updating the transfer function based on the current machine data. The real-time machine data performs system health diagnosis by using an appropriate transfer function(s) and provides further tuning of that transfer function using feedback from the diagnosis of the system with the transfer function.

In another aspect of the present technique, a method of monitoring a medical system (e.g., medical imaging system) includes storing machine parameter data of the medical system, generating a transfer function that correlates a health of the medical system with the stored machine parameter data, and storing the transfer function. The transfer function is automatically updated based on current machine parameter data.

Yet another aspect of the present technique, a method of servicing a medical device including storing a model having a transfer function that correlates a health of the medical device with one or more machine parameters of the medical device, receiving machine data of the medical device, and automatically updating the model based on the machine data. The method may further include diagnosing the health of the medical device via the updated model. Corrective action may be implemented in response to the diagnosis.

In a different aspect of the present technique, a system for maintaining a medical system includes a module configured to generate a transfer function that correlates a health of the medical device with one or more machine parameters of the medical device. The system also includes a module configured to diagnose the medical device via the transfer function, and a module configured to substantially automatically update the transfer function based on contemporaneous machine parameter data.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
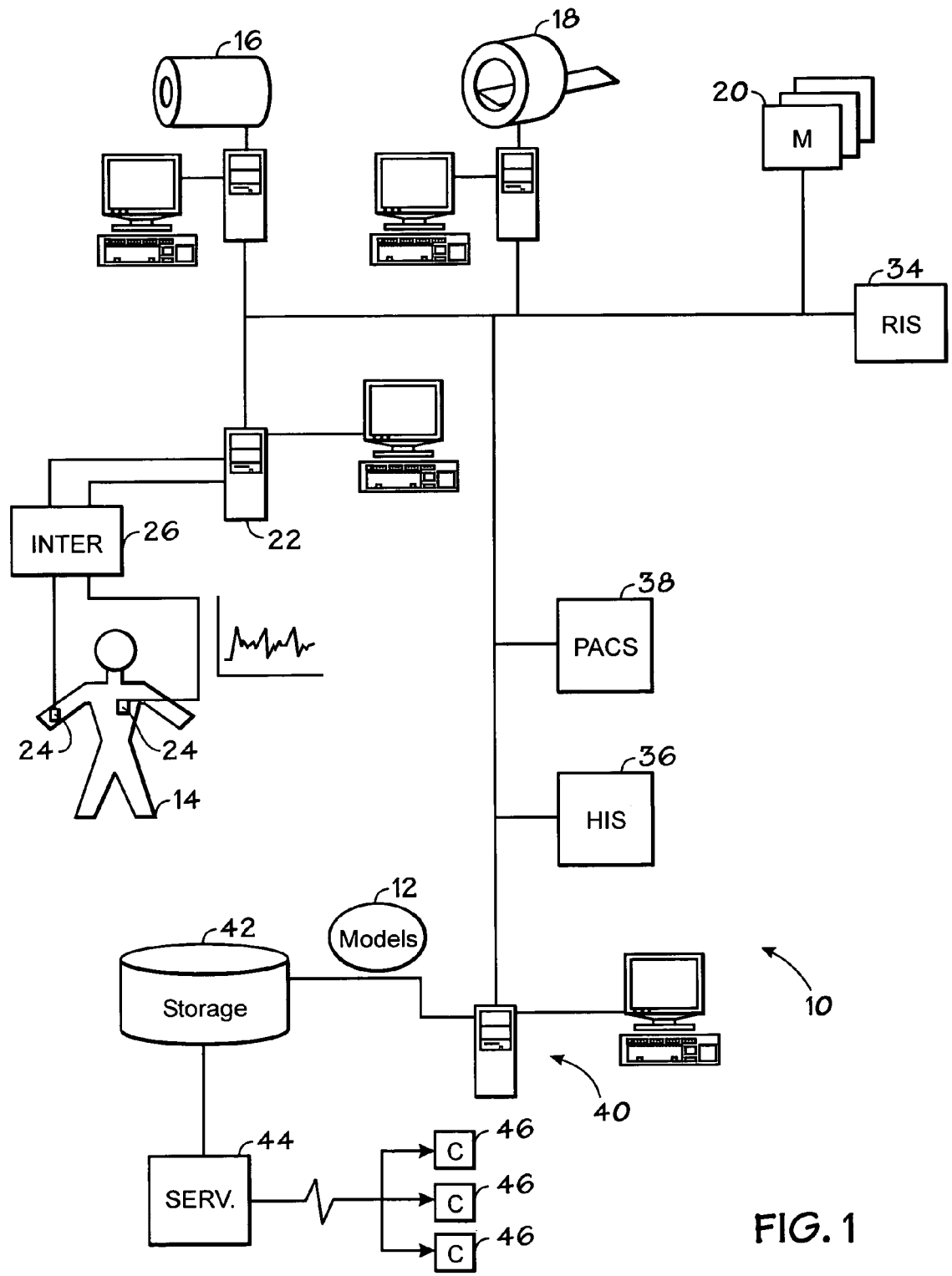
FIG. 1 is simplified diagram a medical facility network having one or more models that correlate the heath and parameters of a medical device in accordance with an exemplary embodiment of the present technique.

The present technique discloses a system and method for generating and automatically updating transfer functions that correlate the health of a medical system or device to parameters of the medical system or device. The technique may take advantage of streams of machine data generated by a medical device (e.g., medical imaging system). Such data may include device usage, error log information, and performance statistics (e.g., related image quality), and so on. The machine data may be stored at the device itself or may be pushed/pulled to a central location (e.g., within the medical facility, at a remote monitoring system such as an online center, and so on). The technique embraces medical systems and devices that generate small or large amounts of machine data. The wealth of data available from the medical devices may be explored and used for improving the health of the medical system or component (e.g., scanner) and increase the productivity and uptime of the medical devices.

Transfer functions are generated that correlate historic (machine) data or parameters of the medical system or device with the health of the device. This relationship between device data (i.e., machine parameters) and the health of the system or device health may be incorporated in a model to be used to monitor and service the device. The transfer functions in the model may be validated for specific medical devices and authenticated by medical device experts and other means. For the subsequent diagnosis of the medical system or device, the transfer functions may be applied to a specific machine to determine the health and maintenance need of that system. This targeted diagnosis may be used to develop a machine specific schedule and action list for maintenance of a specific device or for a device maintenance indicator to determine the health of the current system, a fleet of similar systems, and so on.

Therefore, the technique may utilize a training phase and diagnosis phase. Generation of transfer functions, as well as their validation and authentication, may take place during this initial training phase (e.g., based on historical operating and maintenance data). Subsequently, these transfer functions or models may then be used in the diagnosis of the medical device or system during the latter diagnosis phase. Moreover, during diagnosis of the medical device via the dynamic model, the transfer functions may be further trained or updated. Indeed, during the diagnosis phase, the transfer function may be adjusted and may evolve based on what information is gained from the diagnosis. In fact, the evolution of the model and transfer functions typically continues during the diagnosis phase as the model learns from their usage. Such updating of the transfer functions during the diagnosis phase may be automatic and/or may occur each time a relevant data point is received by the model.

In operation, as the model receives or reads the current machine data, the transfer function within the model is automatically updated to reflect the new data point and its effect on the transfer function(s). Such update to the transfer function may include a variety of changes to the transfer function, such as the adjustment of coefficients, addition/deletion of parameter variables, addition/deletion of parameter interaction components, and the like. Generally, certain variables will be more dominant in the correlation (transfer function) than others at a given instance in the life of the device. Further, a variety of interaction parameters may be generated in the correlation or transfer function. Certain statistical approaches may be utilized to delete variables and interaction parameters to focus the automated transfer function on the variable(s) (machine parameters) having more weight or that is considered critical. Such critical machine parameters are typically more useful in providing the service technician, for example, with useful information as to the device health, image quality, potential for failure, and the like. For machines (e.g., medical devices or systems) that the model predicts have failed or are approaching failure, for example, the present technique may provide for automatic notification of the service technician, such as sending an email or generating a formal request for service.

On the whole, the present technique provides for servicing of medical equipment and systems to tailor to the specific needs of individual machines on a timely and proactive basis. Moreover, the present technique of generating transfer functions that correlate machine parameter data with machine health can be generalized to a variety of medical modalities and devices, as well as non-medical devices. In sum, the technique provides for an effective and economic proactive approach to monitoring and servicing the medical equipment to provide quality performance and increased uptime of the medical system or device.

In one embodiment, a dynamic model correlates the device health or image quality of a medical imaging system with one or more machine parameters. For an exemplary magnetic resonance imaging (MRI) system, as discussed below, the image quality may be a function of the magnet shim and/or signal-to-noise ratio(s) (SNR) within the device. The device health of the MRI may be a function of the machine parameters, such as Head SNR, Body SNR, magnet gradient calculations in three directions, coherent noise, Head stability, Body stability, and so forth.

In a particular example, as discussed below, the analysis involves the evaluation of the rate of change of the magnet center frequency over time. The greater the rate of change of the magnet center frequency, generally the more severe the indication that a problem exists with the magnet shim or magnet field homogeneity of the MRI, and therefore, with the image quality of the MRI images. The dynamic transfer function of the present technique correlates this change in magnet center frequency with drift in magnet shim and the associated magnet field homogeneity (and MRI image quality) to provide for an effective predictive maintenance of the MRI Turning now to the drawings, and referring first to FIG. 1, an overview of a medical facility network 10 utilizing a dynamic model 12 is illustrated. A medical facility data network 10 may include one or more local or remote repositories of medical-related data in a broad sense, as well as interfaces and translators between the repositories, and processing capabilities including analysis, reporting, display and other functions. The repositories and processing resources may be expandable and may be physically resident at any number of locations, typically linked by dedicated or open network links. The flow of information may include a wide range of types and vehicles for information exchange.

In the model 12, as discussed, transfer functions are generated from historical machine data of medical devices to predict the device health of one or more medical systems (e.g., imaging system). Device health may represent, for example, the image quality produced by a medical imaging system, or the operational reliability of the imaging system. Device parameters may include a variety of machine and operational data. The transfer functions may be updated automatically based on current machine parameter data, as well as updated contemporaneously with the receipt of such machine data. The model 12 that correlates the health of a medical device with operational and machine parameters of the medical device may be generated, stored, and automatically updated at various locations in the facility network 10.

In general, a model 12 may include one or more transfer functions that correlate device (machine) health with machine parameters (data). The model 12 and its dynamic transfer functions may be used to predict performance of the device, as well as the appropriate maintenance of the device. A model 12 may provide for improvement of a maintenance schedule of the medical system or device. Indeed, the transfer functions within the model 12 are effective tools to diagnose the health of a medical device. Device specific maintenance may be tailored to the specific device based on its health. The transfer functions are generally device independent yet powerful enough to service the specific device.

A model 12 may be utilized to predict service action for imaging systems, such as a magnetic resonance imaging (MRI) system 16, a computed tomography (CT) imaging system 18, or other modality system 20, such as a vascular imaging system. Other imaging acquisition systems may also utilize a model 12 in the maintenance of the system. Such acquisition systems may include, for example, x-ray imaging systems, positron emission tomography (PET) systems, mammography systems, infrared imaging systems, nuclear imaging systems (e.g., nuclear medicine system), and so forth. Imaging resources are typically available for diagnosing medical events and conditions in both soft and hard tissue, for analyzing structures and function of specific anatomies, and in general, for screening internal body parts and tissue. The components of an imaging system generally include some type of imager which detects signals and converts the signals to useful data. Ultimately, image data may be forwarded to some type of operator interface in the medical facility data network 10 for viewing, storing, and analysis.

In the specific example of an MRI, the imaging system 16 includes a scanner having a primary magnet for generating a magnetic field. A patient is positioned against the scanner and the magnetic field influences gyromagnetic materials within the patient's body. As the gyromagnetic material, typically water and metabolites, attempts to align with the magnetic field, other magnets or coils produce additional magnetic fields at differing orientations to effectively select a slice of tissue through the patient for imaging. As discussed below with regard to FIG. 3, data processing circuitry receives the detected MR signals and processes the signals to obtain data for reconstruction. The resulting processed image data is typically forwarded locally or via a network, to an operator interface for viewing, as well as to short or long-term storage.

Machine parameters of an MRI that may be incorporated in a dynamic transfer function in an exemplary model 12 may include magnet center frequency, for example. The magnet center frequency of an MRI is generally the geometric mean of the upper and lower frequencies of the magnetic field of the MRI. In one example (see FIG. 7), drift of the magnet center frequency (or the rate of change of magnet center frequency) is a machine parameter in the transfer function of the model 12. In this example, the MRI magnet shim (or certain gradients of the shim) is the device health or the output of the transfer function.

Device health factors of an MRI may include magnet shim (or magnet field homogeneity) which is typically an indication of image quality. Operators and service technicians of an MRI may use the transfer function (with magnet center frequency as an input) to predict when the magnet shim (e.g., certain gradients of the magnet shim) will reach a particular value to indicate the onset of unacceptable image quality. An advantage of determining magnet shimming quality instead of observing image quality can be that evaluation of image quality may be subjective.

Shimming corrects inhomogeneity of the magnetic field produced by the main magnet in the MRI. The term shimming originated with the older manual or mechanical process of placing thin pieces of metal (shim stock) under the bolts used to adjust the magnet pole faces in an effort to make the magnet field more homogenous. To improve the ease of manufacturing of MRI's and to improve the capability to correct magnetic field homogeneity after installation of the MRI, an electronic shimming was developed which employs a series of relatively small electromagnets or shim coils to counteract existing magnetic gradients. The approach of adjusting the magnet field homogeneity by adjusting the electrical current in each of these small electromagnets may be called shimming. A service technician may adjust the current in the shim coils by turning knobs, for example, or the MRI may be configured to automatically adjust the current, and so forth In operation, the magnet shim or strength of the various shim coils provides for a homogeneous magnet field, which, in turn, provides for acceptable image quality. The primary magnet in an MRI may be shimmed using the shim coils (electromagnets) with the amount of current to be utilized in shim coils determined via a matrix inversion technique of polynomial expansion of the magnetic field potential, for example. Again, the use of shim coils allows for correction of the field errors introduced in the manufacturing process and is generally standard practice for large MRI magnets. As known in the art, certain electrical shims are low order (e.g., X, Y, Z) while others are higher order having interactions with shims of a similar nature (e.g., ZX creates some Z gradient and X gradient in addition to the intended ZX gradient). Because of these interactions, the number of adjustments employed to shim the MRI magnet generally increases geometrically, not linearly.

For the example of the modality of a CT imaging system 18, the basic components include a radiation source and detector. As explained below with regard to FIG. 4, during an examination sequence, as the source and detector are rotated, a series of view frames are generated at angularly-displaced locations around a patient 14 positioned within a gantry. A number of view frames (e.g. between 500 and 1000) may be collected for each rotation. For each view frame, data is collected from individual pixel locations of the detector to generate a large volume of discrete data. Data collected by the detector is digitized and forwarded to data acquisition and processing circuitries, which process the data and generate a data file accessible, for example on a medical facility data network.

Machine parameters of a CT imaging system 18 that may be incorporated in a dynamic transfer function in an exemplary model 12 may include cumulative total milliamps and/or kilowatt-hours of the operating CT system 18, cumulative number of slices, cumulative scan time, and so on. The cumulative aspect of these variables may be reset upon maintenance of the CT system 18. Device health factors of a CT imaging system 18 may include equipment failure, such as a tube failure, for example. In other words, the model 12 via the machine parameters may predict when a part (e.g., tube) of the CT imaging system 18 will fail or is at some percent probability (e.g., 50%, 75%, etc.) of failing. Moreover, tube failures may be related to or caused by, for example, loss of vacuum in the tube, aging or failure of the filament within the tube, voltage spikes, humidity, and so forth. Failure of the tube is generally readily apparent because, in part, such failure results in the generation of black images. Typically, the tube is replaced upon its failure.

As indicated, other imaging and medical systems 20 may utilize a model 12, such as vascular and interventional imaging systems which may rely on radioactivity and/or fluorescence, for example, to image (i.e., via an X-ray detector) the cardiovascular system (i.e., coronary arteries, cardiac chambers, etc.). In certain applications, such as with digital fluorography, relatively large-format digital flat panel detectors may be employed in the X-ray system for high resolution angiographic imaging. These systems may allow for imaging of vascular detail across various tissue densities in the chest, neck, abdomen, or peripheral the body. Indeed, with a large detector, the entire body may be imaged. Moreover, fine vessel detail (up to the skin surface) of extremities may be viewed in certain applications.

Fluoroscopic or fluorography (or vascular) systems may consist of X-ray image intensifiers coupled to photographic and video cameras. As indicated, digital detectors such as those used on digital X-ray systems are also used in such fluoroscopic systems. The collected data may be recorded for later reconstruction into a moving picture-type display. Such techniques are sometimes referred to as cine-fluorography. Such procedures are widely used in cardiac studies, such as to record movement of a living heart. Again, the studies may be performed for later reference, or may also be performed during an actual real-time surgical intervention. As in conventional X-ray systems, the camera used for fluorography systems receives a video signal which is collected by a video monitor for immediate display. A video tape or disk recorder may be used for storage and later playback. The computer system or data processing circuitry may perform additional processing and analysis on the image data both in real-time and subsequently.

In general, the various techniques used in fluorography or vascular systems may be referred to as video-fluoroscopy or screening, and digital fluorography. The latter technique is replacing many conventional photography-based methods and is sometimes referred to as digital spot imaging (DSI), digital cardiac imaging (DCI) and digital vascular imaging (DVI)/digital subtraction angiography (DSA), depending upon the particular clinical application. A hard-copy device, such as a laser imager, is used for to output hard copies of digital images. Moreover, fluoroscopic techniques may be used in conjunction with conventional X-ray techniques, particularly where a digital X-ray detector is employed as described above. That is, high-energy X-ray images may be taken at intervals interspersed with fluoroscopic images, the X-ray images providing a higher resolution or clarity in the images, while the fluoroscopic images provide real-time movement views.

Machine parameters of a fluorography or vascular system that may be incorporated in a dynamic transfer function in an exemplary model 12 may include cumulative "fluoro" time (i.e., X-ray scan time), cumulative power-on time, anode spits, cathode spits, combined anode and cathode spits, cumulative energy on small and/or large filaments, temperature of electronics, anode accelerations, cumulative milliamps, and the like. Such variables may be evaluated over time, for example, to determine when a component of the vascular system will fail, or to predict when a sensor (e.g., collision sensor for collision of detector and gantry, etc.) will activate and shut down the vascular system, and so on. The evaluation of the variables over time may involve the absolute values of the variables and/or their rate of change (slope), as well as the mean, maximum (peak), counts per day, and the like. Moreover, as appreciated by those of ordinary skill in the art, various statistical sampling techniques may be employed, such as plotting individual and/or aggregate operators, and so forth.

Other imaging and medical systems 20 may also utilize a model 12. In the illustrative embodiment of FIG. 1, a model 12 or transfer function may be generated, stored, and automatically updated by a computer system 22 that collects sensor/monitor 24 data via an interface 26. This configuration may include, for example, a variety of data collection systems designed to detect physiological parameters of patients based upon sensed signals. Resulting output data may be stored in the computer system 22 and/or at other repositories or storage sites linked to the medical facility data network, and utilized in the construction and update of a model 12.

In particular, system 20 may include electrical data resources and modalities, such as electroencephalography (EEG), electrocardiography (ECG or EKG), electromyography (EMG), electrical impedance tomography (EIT), nerve conduction test, electronystagmography resources (ENG), combinations of such modalities, and so forth. For the example of electrical modalities or resources, components typically include sensors or transducers, such as sensor/monitors 24, which may be placed on or about a patient 14 to detect certain parameters of interest that may be indicative of medical events or conditions. Thus, the sensors 24 may detect electrical signals emanating from the body or portions of the body, pressure created by certain types of movement (e.g. pulse, respiration), or parameters such as movement, reactions to stimuli, and so forth. The sensors 24 may be placed on external regions of the body, but may also include placement within the body, such as through catheters, injected or ingested means, and so forth. Machine parameters of electrical data modalities that may be incorporated in a transfer function in an exemplary model 12 may include run time of the equipment, and so forth. Device health factors of electrical data modalities may include failure of the equipment, and so on.

In general, machine information, images, and the like may be stored in an institution within a radiology information system (RIS) 34 and/or hospital information system (HIS) 36. Many institutions further store and evaluate data, particularly image data, in archiving systems, commonly referred to as PACS 38 in the form of compressed and uncompressed image data. A workstation 10 may be used to communicate with the network 40 and to construct the dynamic models 12 or transfer functions, which may stored in storage 42, such as a hard drive or other storage device. A server 44 may provide access to the models 12 to remote clients 46.

Figure 2:
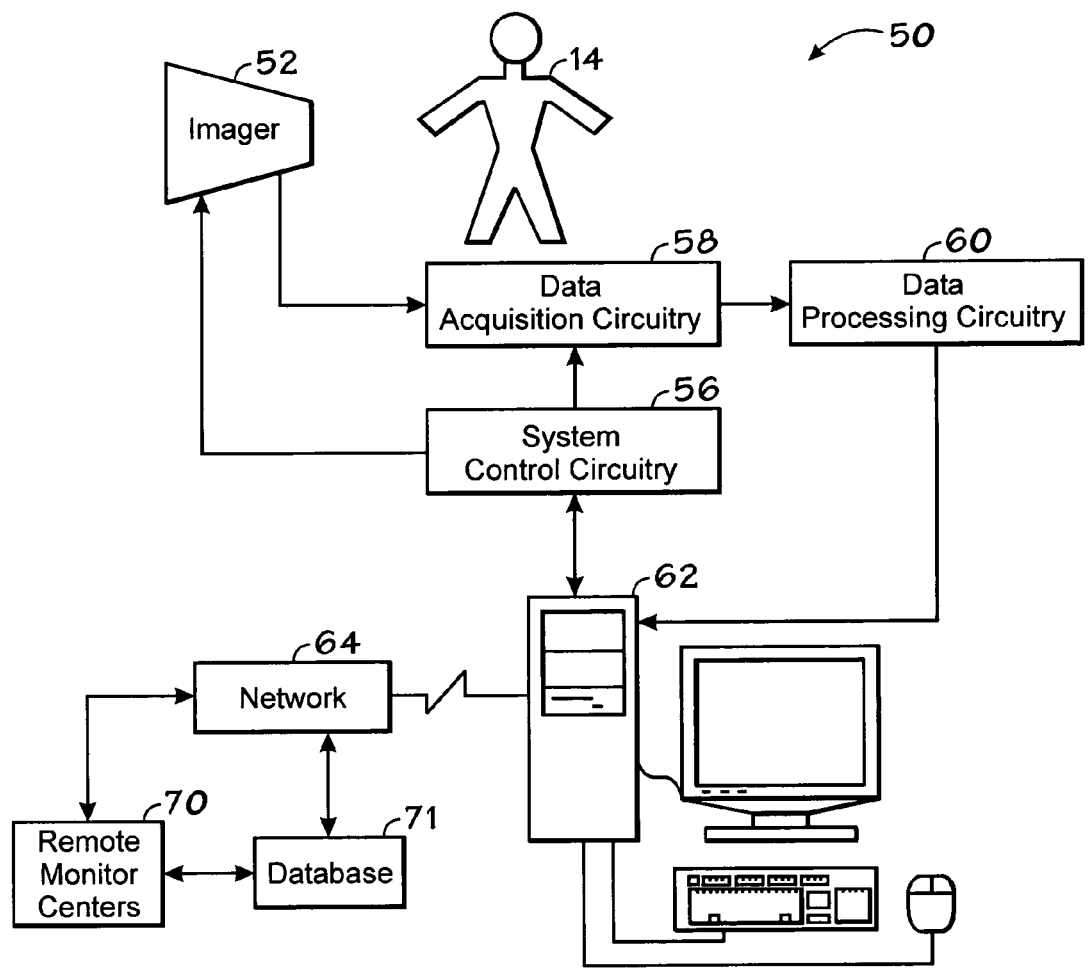
FIG. 2 is a is a general diagrammatical representation of certain functional components of an exemplary medical imaging system, in accordance with an exemplary embodiment of the present technique.

FIG. 2 depicts a generic imaging system 50 (e.g., MRI, CT, etc.) which may be representative of a variety of imaging modalities and which may be monitored and serviced via the dynamic models 12. Operating information about the various components depicted may be incorporated machine parameter data and device health data for the dynamic models 12. An imaging system 10 generally includes some type of imager 12 which detects signals and converts the signals to useful data. As described more fully below, the imager 12 may operate in accordance with various physical principles for creating the image data. In general, however, in image data indicative of regions of interest in a patient 14 are created by the imager either in a conventional support, such as photographic film, or in a digital medium.

The imager 52 operates under the control of system control circuitry 56. The system control circuitry may include a wide range of circuits, such as radiation source control circuits, timing circuits, circuits for coordinating data acquisition in conjunction with patient or table of movements, circuits for controlling the position of radiation or other sources and of detectors, and so forth. The imager 52, following acquisition of the image data or signals, may process the signals, such as for conversion to digital values, and forwards the image data to data acquisition circuitry 58.

In the case of analog media, such as photographic film, the data acquisition system may generally include supports for the film, as well as equipment for developing the film and producing hardcopies that may be subsequently digitized. For digital systems, the data acquisition circuitry 58 may perform a wide range of initial processing functions, such as adjustment of digital dynamic ranges, smoothing or sharpening of data, as well as compiling of data streams and files, where desired. The data are then transferred to data processing circuitry 60 where additional processing and analysis are performed. For conventional media such as photographic film, the data processing system may apply textual information to films, as well as attach certain notes or patient-identifying information. For the various digital imaging systems available, the data processing circuitry 60 may perform substantial analyses of data, ordering of data, sharpening, smoothing, feature recognition, and so forth.

Ultimately, the image data are forwarded to some type of operator interface 62 for viewing and analysis. The image data can also be transferred to remote locations, such as via a network 64. It should also be noted that, from a general standpoint, the operator interface 62 affords control of the imaging system, typically through interface with the system control circuitry 56. Moreover, it should also be noted that more than a single operator interface 62 may be provided. Accordingly, an imaging scanner or station may include an interface which permits regulation of the parameters involved in the image data acquisition procedure, whereas a different operator interface may be provided for manipulating, enhancing, and viewing resulting reconstructed images.

In some circumstances, images acquired on conventional media, such as photographic film, may be converted to digitized images via an analog-to-digital converter, such as a digitizer, scanner, and the like. These digitized images or files may be digitally stored locally at the operator interface 62 or at other memory locations via network 64. It is typical, for example, for conventional film to be scanned in the sheet mode.

Remote monitoring centers 70 may have access to the imaging system 50 and its workstation 62 via the network 64. The remote monitoring center may have access to machine parameter data, device health information, and other information within the imaging system 50, on the workstation 62, in a separate database 71, on the medical facility network 10 (see FIG. 1), and so forth. The remote monitoring centers 70 may monitor the imaging system 50 via the model 12 having the automatically-updated transfer functions. The centers 70 may also remotely service the imaging system 50, where possible. As indicated, data regarding the various components and operations of an imaging system 50 discussed above may be employed in a transfer function of a model 12 to determine the device health and the appropriate servicing of the imaging system 50.

Two specific medical imaging modalities based upon the overall system architecture outlined in FIG. 2 are discussed below. The two modalities, magnetic resonance imaging (MRI) and computed tomography (CT) imaging, may be monitored and serviced, for example, via the models 12 of the present technique. The two modalities are given only as examples, and it should be apparent that the present technique may apply to a variety of imaging modalities and applications.

Figure 3:
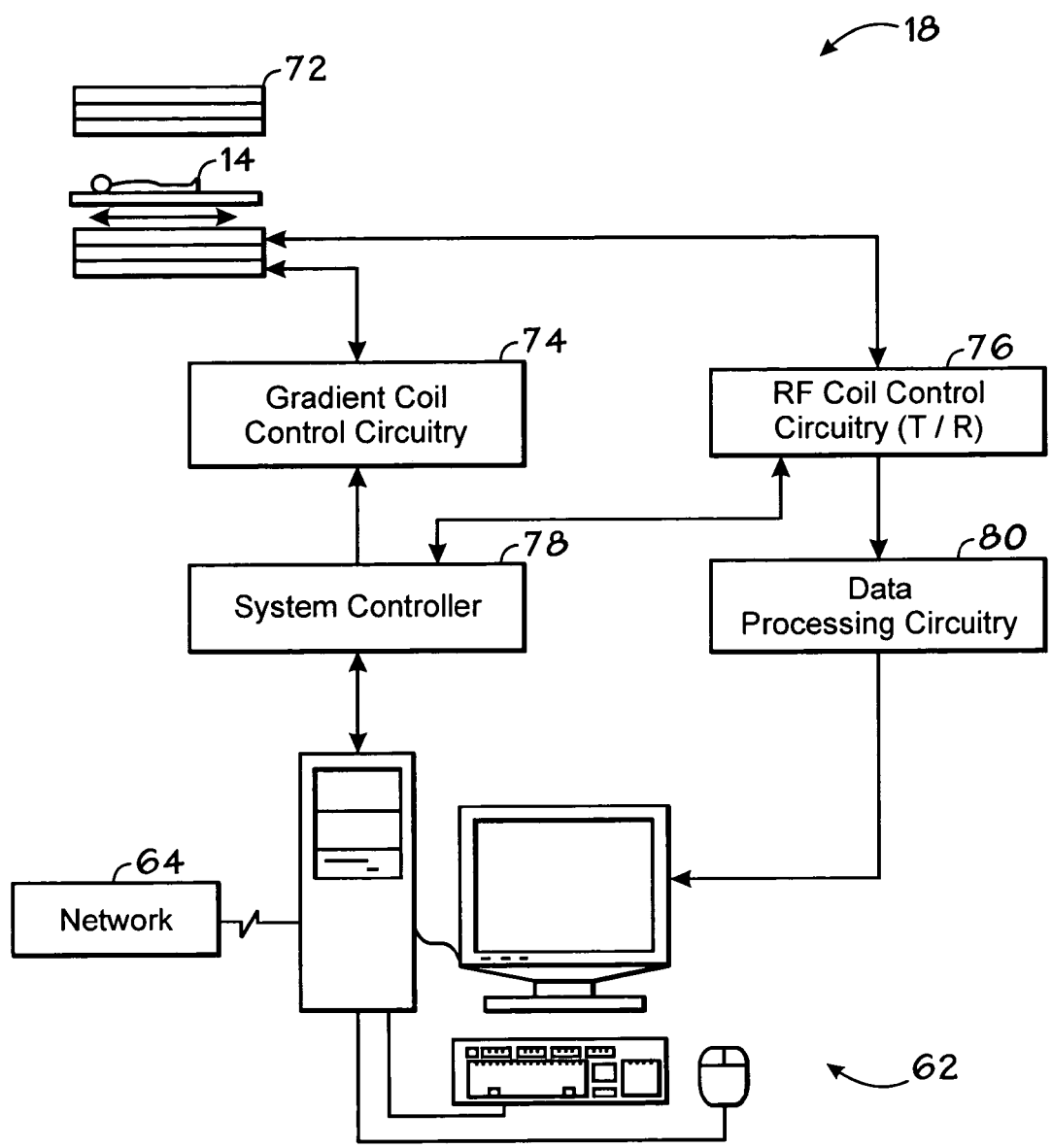
FIG. 3 is a diagrammatical representation of a particular imaging system of the type shown in FIG. 1, in this case an exemplary magnetic resonance (MR) imaging system in accordance with an exemplary embodiment of the present technique.

FIG. 3 represents a general diagrammatical representation of a magnetic resonance imaging system 18. The system includes a scanner 72 in which a patient 14 is positioned for acquisition of image data. The scanner 72 generally includes a primary magnet and gradient coils for generating a magnetic field which influences gyromagnetic materials within the patient's body. As the material attempts to align with the magnetic field, gradient coils produce additional magnetic fields which are orthogonally oriented with respect to one another. As discussed, the gradient fields effectively select a slice of tissue through the patient for imaging, and encode the gyromagnetic materials within the slice in accordance with phase and frequency of their rotation. Again, a radio-frequency (RF) coil in the scanner generates high frequency pulses to excite the gyromagnetic material and, as the material attempts to realign itself with the magnetic fields, magnetic resonance signals are emitted which are collected by the radio-frequency coil.

The scanner 72 is coupled to gradient coil control circuitry 74 and to RF coil control circuitry 76. The gradient coil control circuitry permits regulation of various pulse sequences which define imaging or examination methodologies used to generate the image data. Pulse sequence descriptions implemented via the gradient coil control circuitry 74 are designed to image specific slices, anatomies, as well as to permit specific imaging of moving tissue, such as blood, and defusing materials. The pulse sequences may allow for imaging of multiple slices sequentially, such as for analysis of various organs or features, as well as for three-dimensional image reconstruction. The RF coil control circuitry 76 permits application of pulses to the RF excitation coil, and serves to receive and partially process the resulting detected MR signals. It should also be noted that a range of RF coil structures may be employed for specific anatomies and purposes. In addition, a single RF coil may be used for transmission of the RF pulses, with a different coil serving to receive the resulting signals.

The gradient and RF coil control circuitry function under the direction of a system controller 78. The system controller implements pulse sequence descriptions which define the image data acquisition process. The system controller will generally permit some amount of adaptation or configuration of the examination sequence by means of the operator interface 62, which may be coupled (e.g., via the Internet) to a remote monitoring center 70 and/or database, as depicted in FIG. 2.

Data processing circuitry 80 receives the detected MR signals and processes the signals to obtain data for reconstruction. In general, the data processing circuitry 80 digitizes the received signals, and performs a two-dimensional fast Fourier transform on the signals to decode specific locations in the selected slice from which the MR signals originated. The resulting information provides an indication of the intensity of MR signals originating at various locations or volume elements (voxels) in the slice. Each voxel may then be converted to a pixel intensity in image data for reconstruction. The data processing circuitry 80 may perform a wide range of other functions, such as for image enhancement, dynamic range adjustment, intensity adjustments, smoothing, sharpening, and so forth. The resulting processed image data is typically forwarded to an operator interface for viewing, as well as to short or long-term storage. As in the case of foregoing imaging systems, MR image data may be viewed locally at a scanner location, or may be transmitted to remote locations both within an institution and remote from an institution such as via network 64. Data regarding the various components and operations of the MRI system 18 discussed above may be employed in one or more transfer functions of a dynamic model 12 to determine the device health and the appropriate servicing of the MRI system 18.

Figure 4:
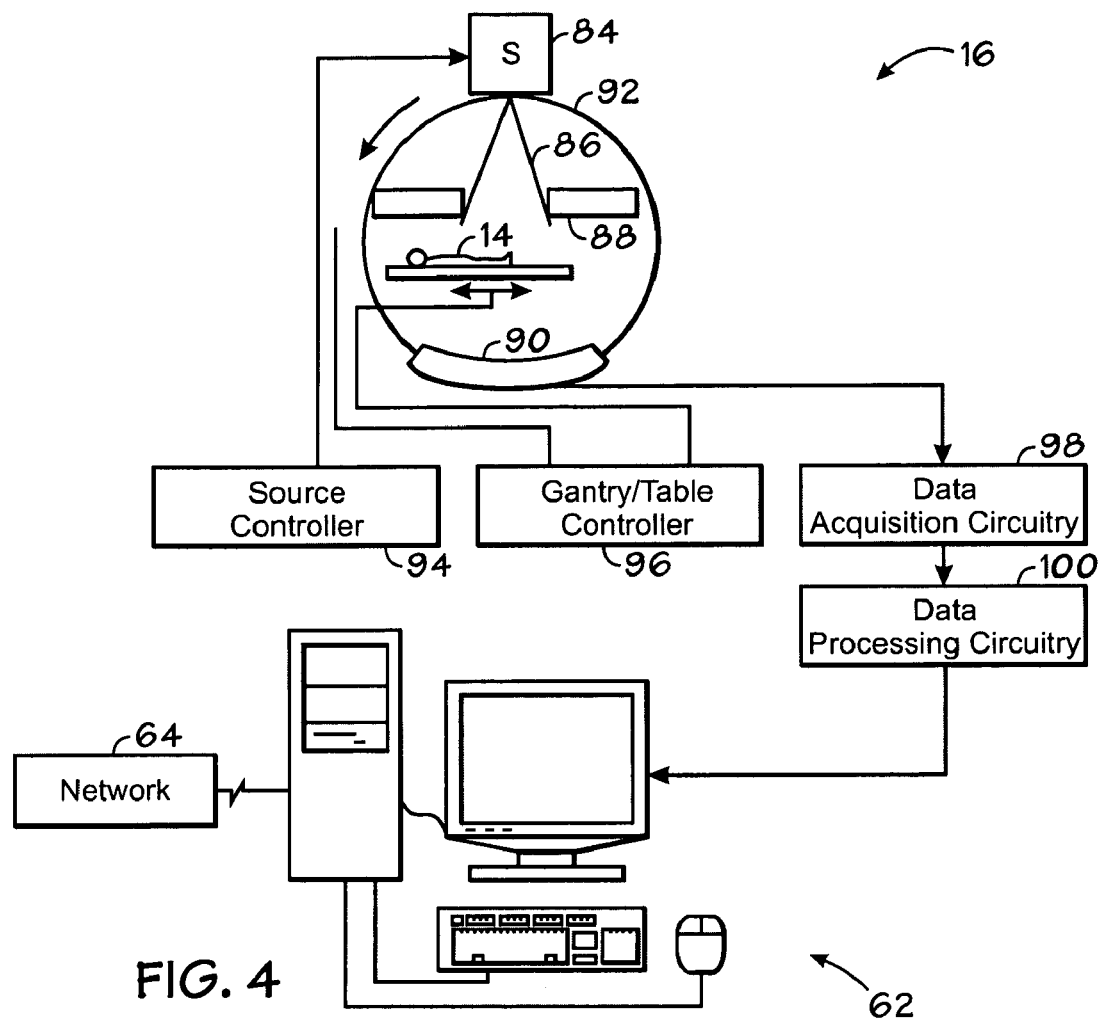
FIG. 4 is a diagrammatical representation of a particular imaging system of the type shown in FIG. 1, in this case an exemplary computed tomography (CT) imaging system in accordance with an exemplary embodiment of the present technique.

FIG. 4 illustrates the basic components of a computed tomography (CT) imaging system. The CT imaging system 16 includes a radiation source 84 which is configured to generate X-ray radiation in a fan-shaped beam 86. A collimator 88 defines limits of the radiation beam. The radiation beam 86 is directed toward a curved detector 90 made up of an array of photodiodes and transistors which permit readout of charges of the diodes depleted by impact of the radiation from the source 84. The radiation source, the collimator and the detector are mounted on a rotating gantry 92 which enables them to be rapidly rotated (such as at speeds of two rotations per second).

During an examination sequence, as the source and detector are rotated, a series of view frames are generated at angularly-displaced locations around a patient 14 positioned within the gantry. As mentioned, a number of view frames (e.g. between 500 and 1000) are collected for each rotation, and a number of rotations may be made, such as in a helical pattern as the patient is slowly moved along the axial direction of the system. For each view frame, data is collected from individual pixel locations of the detector to generate a large volume of discrete data. A source controller 94 regulates operation of the radiation source 84, while a gantry/table controller 96 regulates rotation of the gantry and control of movement of the patient.

Again, data collected by the detector is digitized and forwarded to a data acquisition circuitry 98. The data acquisition circuitry may perform initial processing of the data, such as for generation of a data file. The data file may incorporate other useful information, such as relating to cardiac cycles, positions within the system at specific times, and so forth. Data processing circuitry 100 then receives the data and performs a wide range of data manipulation and computations.

In general, data from the CT scanner can be reconstructed in a range of manners. For example, view frames for a full 360° of rotation may be used to construct an image of a slice or slab through the patient. However, because some of the information is typically redundant (imaging the same anatomies on opposite sides of a patient), reduced data sets comprising information for view frames acquired over 180° plus the angle of the radiation fan may be constructed. Alternatively, multi-sector reconstructions are utilized in which the same number of view frames may be acquired from portions of multiple rotational cycles around the patient. Reconstruction of the data into useful images then includes computations of projections of radiation on the detector and identification of relative attenuations of the data by specific locations in the patient. The raw, the partially processed, and the fully processed data may be forwarded for post-processing, storage and image reconstruction. The data may be available immediately to an operator, such as at an operator interface 62, and may be transmitted remotely via network 64 (e.g., to a remote monitoring center 70 and/or database 71, as depicted in FIG. 2). Data regarding the various components and operations of the MRI system 18 discussed above may be employed in one or more transfer functions of a dynamic model 12 to determine the device health and the appropriate servicing of the MRI system 18.

Indeed, for imaging systems, such as the CT and MRI systems discussed above, the present technique may be employed to monitor the machine parameters and device health of the systems via the exemplary models 12 (see FIG. 1). The various individual components and circuitry of the imaging systems may be monitored and service (local and/or remote). The present technique enhances the predictive maintenance of the imaging systems, providing for more economical service and less downtime, for example.

Figure 5:
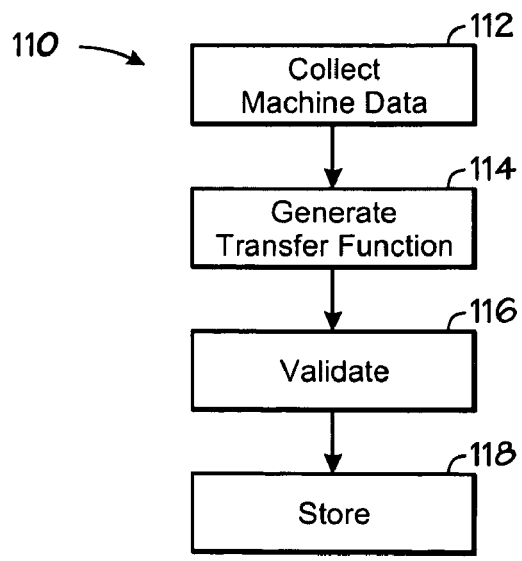
FIG. 5 is a flow chart illustrating an exemplary method of generating a transfer function in the training phase of a model in accordance with an exemplary embodiment of the present technique.

FIG. 5 is a flow chart of an exemplary method 110 of generating or determining a transfer function in the training phase of a model 12. As discussed, the present technique typically utilizes a training phase that generally employs historical data to develop the transfer function(s) for the associated model 12 prior to implementation of the model in a diagnosis phase in which the medical device is monitored via the model 12. Moreover, the training or developing of the dynamic model 12 may be updated during the training phase.

In an exemplary training phase, historical data of machine parameters, historical data of machine (device) health and maintenance/service, and the like, are collected, as indicated in block 112. Such data may be available within a medical facility network or database, and/or directly from the medical device or modality, for example. Based on the collected historical data (block 112), at least one transfer function is generated that correlates device health with machine parameters, as indicated in block 114. During the training phase, the generated transfer functions may be validated (block 116) and stored (block 118), as discussed above.

Figure 6:
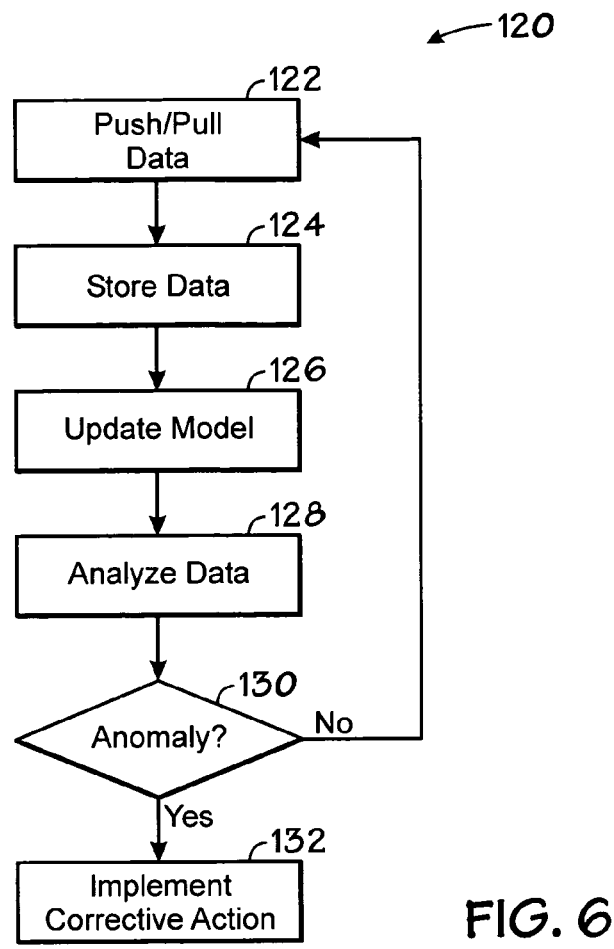
FIG. 6 is a flow chart illustrating an exemplary process of updating a transfer function in the diagnosis phase of a model in accordance with an exemplary embodiment of the present technique.

FIG. 6 is a flow chart of an exemplary method 120 of operating and updating a dynamic model 12 during the diagnosis phase. In the illustrated embodiment, machine parameter data are received from the medical device/system or from a database, for example, as indicated by block 122. The data may be pushed by the medical device and/or the data may be pulled by the computer system (e.g., workstation, server, laptop, etc.) employed to run the model 12. The dynamic model 12 may disposed remotely, such as at a remote on-line service center. On the other hand, the model 12 may be located in the same facility as the device being monitored (e.g., stored on a facility network), or disposed on a workstation of the medical system or modality itself, for example. The received data, whether pushed or pulled, may be stored, as indicated in block 124.

Upon receipt of the data or at some point in time thereafter, the transfer function(s) of the model 12 may be updated (e.g., revisions of coefficients, addition/deletion of parameters, etc.), as discussed above, and as referenced in block 126. Generally, the transfer function of the dynamic model 12 is updated as the machine data is received, and therefore, may be considered a dynamic model 12. Conversely, the model 12 may also be updated at specified time intervals or based on other criteria, and therefore may be considered quasi-dynamic (i.e., not fully static).

In its monitoring capacity of the diagnosis phase, the model 12 analyzes the data received and supporting the model 12 is analyzed (block 128). Based on the analysis (and sometimes other factors), the dynamic model 12 determines via the dynamic transfer function if an anomaly (e.g., a potential failure of the medical device, a malfunctioning component of the device, poor image quality, etc.) exists. If so, model 12 and its associated system may notify a service technician (e.g., via an email or page), or activate an alarm, for example. In certain embodiments, the model 12 may simply store indication of the anomaly for later retrieval by an operator or service technician. In response to the indication via a notification, description, etc. of the anomaly, corrective action may be implemented, as indicated by blocks 130 and 132. As discussed above, such corrective action may include replacement of a component of the medical system or device, calibration of the device, and so forth.

Figure 7:
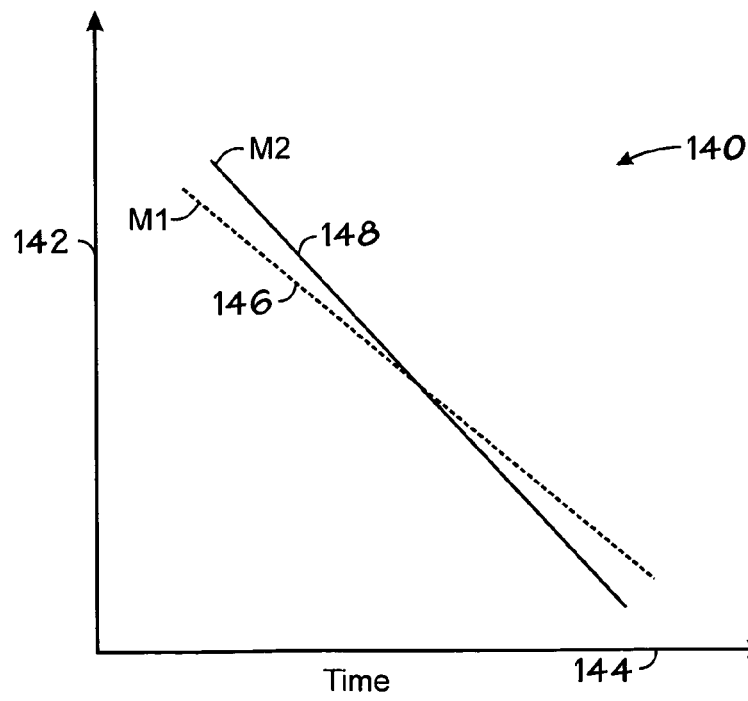
FIG. 7 is a plot of magnet center frequency of a magnetic resonance imaging (MRI) system over time in accordance with an exemplary embodiment of the present technique.

FIG. 7 is a plot 140 of magnet center frequency 142 of a magnetic resonance imaging (MRI) system over time 144. The plot 140 is representative of the analysis within a dynamic model 12 and the associated monitoring of a medical device, the given MRI. In this example, the transfer function, as currently updated, incorporates a single input machine parameter or variable, the magnet center frequency 146 of the MRI. This exemplary transfer function relies on the rate of change of the magnet center frequency over time as the input. In this analysis, the output parameter or variable indicative of the MRI performance is the magnet shim or certain gradients of the magnet shim (not illustrated). The correlation or transfer function of the model 12, based on the MRI magnet center frequency as an input, is used to predict when the magnet shim or gradients of the magnet shim becomes unacceptable, indicating poor image quality.

Again, it is how the magnet frequency changes with time that is used to predict when the magnet shim will become or has become undesirable, and therefore, when the magnet field inhomogeneity has become too great (and the image quality poor). In the illustrated embodiment, the magnet center frequency is decreasing over time, and therefore, has a negative slope. In the present state of the dynamic transfer function of the model 12, the more negative the slope and higher the change in rate of slope, the greater the chance of distorted magnet shim values which may be associated with excessive inhomogeneity in the magnetic field and poor image quality.

In this illustrated case, the rate of change over time is increasing in time (i.e., from M1 to M2), as indicated by lines 146 and 148. Each time a new data point of magnet center frequency is received by the model 12, the data are linearly re-fit and a new slope calculated. In this example, the M1 and M2 are two slopes at two different points in time, with M2 as a later point in time. Therefore, the slope is increasing (in a negative direction) in time. When the change in slope reaches a predetermined value (e.g., greater than −3.0 hertz per day), the service technician will be notified to repair the MRI machine. The repair may involve shimming the magnet, changing the magnet, and so on.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of maintaining a medical device, comprising:
generating a transfer function correlating historical machine data with a health of the medical device;
validating and storing the transfer function;
receiving current machine data of the medical device in substantially real time; and
automatically updating the transfer function based on the current machine data.

2. The method according to claim 1, wherein automatically updating comprises updating the transfer function substantially contemporaneously with receipt of the current machine data.

3. The method according to claim 1, wherein automatically updating comprising updating the transfer function during monitoring and diagnosis of the medical device.

4. The method according to claim 1, comprising detecting an anomaly of the medical device via the transfer function.

5. The method according to claim 4, comprising implementing corrective action in response to the detection of the anomaly.

6. A method of monitoring a medical system, comprising:
storing machine parameter data of the medical system;
generating a transfer function that correlates a health of the medical system with the stored machine parameter data;
storing the transfer function; and
automatically updating the transfer function based on current machine parameter data.

7. The method according to claim 6, comprising storing and updating the transfer function at a location remote from the medical system.

8. The method according to claim 6, comprising storing or updating the transfer function on a portable computer system.

9. The method according to claim 6, comprising servicing the medical system in response to diagnosis of the medical system via the updated transfer function.

10. A method of servicing a medical device, comprising:
storing a model having a transfer function that correlates a health of the medical device with one or more machine parameters of the medical device;
receiving machine data of the medical device; and
automatically updating the model based on the machine data.

11. The method according to claim 10, wherein storing comprises storing the model on the medical device or in a remote service center, or a combination thereof.

12. The method according to claim 10, comprising diagnosing the health of the medical device via the updated model.

13. The method according to claim 12, wherein diagnosing comprises diagnosing the health of the device locally or remotely, or a combination thereof.

14. The method according to claim 12, comprising implementing corrective action in response to the diagnosis.

15. The method according to claim 12 wherein the medical device comprises a medical imaging system.

16. The method according to claim 12, wherein the medical device comprises a magnetic resonance imaging system (MRI) and the one or more machine parameters comprise magnet center frequency.

17. The method according to claim 16, wherein the device health comprises a gradient of magnet shim.

18. The method according to claim 17, comprising adjusting the magnet shim in response to analysis of machine data via the transfer function.

19. A system for maintaining a medical system, comprising:
a module configured to generate a transfer function that correlates a health of the medical device with one or more machine parameters of the medical device;
a module configured to diagnose the medical device via the transfer function; and a module configured to substantially automatically update the transfer function based on contemporaneous machine parameter data.

20. The system of claim 19, comprising a module configured to notify an operator or service technician.

21. The system according to claim 19, wherein the medical device comprises a CT system, a vascular imaging system, or a nuclear medicine system, or any combination thereof.

22. A computer program, provided on one or more tangible media, for maintaining a medical device, comprising:

a routine for generating a transfer function that correlates a health of the medical device with one or more machine parameters of the medical device;

a routine for diagnosing the medical device via the transfer function; and a routine for automatically updating the transfer function based on machine parameter data received during diagnosis of the medical device.

23. The computer program of claim 22, comprising a routine for notifying an operator or service technician.

* * * * *